United States Patent
Watanabe et al.

(10) Patent No.: US 11,518,729 B2
(45) Date of Patent: Dec. 6, 2022

(54) PROCESSES FOR PREPARING 5,5-DIMETHYL-2-OXO-3-CYCLOPENTENE-1-CARBOXYLATE COMPOUNDS AND 3,5,5-TRIMETHYL-2-OXO-3-CYCLOPENTENE-1-CARBOXYLATE COMPOUNDS FROM 3,3-DIMETHYL-1-BUTENE-1,4-DICARBOXYLATE COMPOUNDS AND 1,3,3-TRIMETHYL-1-BUTENE-1,4-DICARBOXYLATE COMPOUNDS, AND 1,3,3-TRIMETHYL-1-BUTENE-1,4-DICARBOXYLATE COMPOUNDS

(71) Applicant: Shin-Etsu Chemical Co., Ltd., Tokyo (JP)

(72) Inventors: Tomohiro Watanabe, Niigata (JP); Takeshi Kinsho, Niigata (JP); Miyoshi Yamashita, Niigata (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 17/378,936

(22) Filed: Jul. 19, 2021

(65) Prior Publication Data
US 2022/0024846 A1 Jan. 27, 2022

(30) Foreign Application Priority Data
Jul. 22, 2020 (JP) .............................. JP2020-125810

(51) Int. Cl.
C07C 67/327 (2006.01)
C07C 69/593 (2006.01)
C07C 67/313 (2006.01)

(52) U.S. Cl.
CPC .......... *C07C 67/327* (2013.01); *C07C 67/313* (2013.01); *C07C 69/593* (2013.01); *C07C 2601/10* (2017.05)

(58) Field of Classification Search
None
See application file for complete search history.

(56) References Cited

U.S. PATENT DOCUMENTS

2021/0206711 A1   7/2021   Chebny

OTHER PUBLICATIONS

Cocker ("The Chemistry of Terpenes. Part XVII. Synthesis of (+)-cis-Homo-caronic Acid (cis-3-Carboxymethyl-2,2-dimethylcyclopropanecarboxylic Acid) and Some Related Compounds" J. C. S. Perkin I, 1974, p. 194-202) (Year: 1974).*
Crowley ("Photoisomerizations. X. The Photochemical Transformations of Alloocimene" J. Org. Chem. 1968, p. 3679-3686) (Year: 1968).*
Huisgen ("Cycloadditions to Methyl 3,3-Dimethyl-3H-pyrazole-5-carboxylate" J.C.S. Chem. Comm. 1979, p. 568-570) (Year: 1979).*
Figadère et al. "trans-α-Necrodyl isobutyrate, the sex pheromone of the grape mealybug, *Pseudococcus maritimus*" Tetrahedron Letters, 48:8434-8437 (2007).
Franco et al. "Novel Approaches for the Management of Mealybug Pests" Biorational Control of Arthropod Pests, 233-278 (2009).
Jacobs et al. "Defense mechanisms of arthropods. 84. Synthesis of (-)-α-necrodol and (-)-β-necrodol: Novel cyclopentanoid terpenes from a carrion beetle" Journal of Organic Chemistry, 55:4051-4062 (1990).
Millar et al. "Chemistry and Applications of Mealybug Sex Pheromones" Semiochemicals in Pest and Weed Control, Chapter 2, pp. 11-27 (2005).
Ross et al. "Scale insects" Current Biology, 19(5):R184-R186 (2009).
Tabata et al. "Sex pheromone of a coccoid insect with sexual and asexual lineages: fate of an ancestrally essential sexual signal in parthenogenetic females" Journal of the Royal Society Interface, 14:1-11 (2017).
Tabata et al. "Sexual attractiveness and reproductive performance in ageing females of a coccoid insect" Biology Letters, 14:1-5 (2018).
Zou et al. "Chemistry of the pheromones of mealybug and scale insects" Natural Product Reports, 32:1067-1113 (2015).
Levi-Zada et al. "Identification of the Sex Pheromone of the Spherical Mealybug *Nipaecoccus viridi*" Journal of Chemical Ecology, 45:455-463 (2019).
Richers et al. "Synthesis and Neurotrophic Activity Studies of Illicium Sesquiterpene Natural Product Analogues" Chemistry A European Journal, 23:3178-3183 (2017).

(Continued)

*Primary Examiner* — Amy C Bonaparte
(74) *Attorney, Agent, or Firm* — Myers Bigel, P.A.

(57) ABSTRACT

The present invention provides a process for preparing a compound of the following general formula (2): wherein $R^1$ represents a monovalent hydrocarbon group having 1 to 10 carbon atoms, and $R^3$ represents a hydrogen atom or a methyl group, the process comprising: subjecting a compound of the following general formula (1): wherein $R^1$ and $R^2$ represent, independently of each other, a monovalent hydrocarbon group having 1 to 10 carbon atoms, $R^3$ represents a hydrogen atom or a methyl group, and the wavy bond represents an E-configuration, a Z-configuration, or a mixture thereof, to a Dieckmann condensation in the presence of base to form the compound (2).

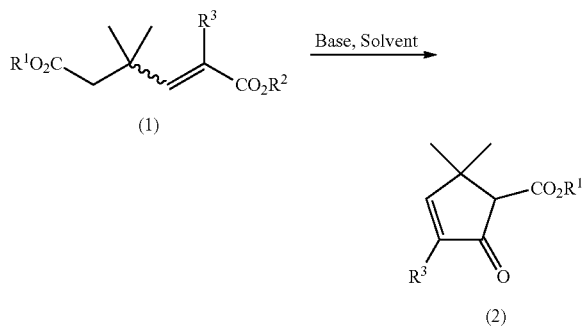

5 Claims, No Drawings

(56) References Cited

OTHER PUBLICATIONS

Zou et al. "Synthesis and Bioassay of Racemic and Chiral trans-alpha-Necrodyl Isobutyrate, the Sex Pheromone of the Grape Mealybug *Pseudococcus maritimus*" Journal of Agricultural and Food Chemistry, 58:4977-4982 (2010).

* cited by examiner

PROCESSES FOR PREPARING 5,5-DIMETHYL-2-OXO-3-CYCLOPENTENE-1-CARBOXYLATE COMPOUNDS AND 3,5,5-TRIMETHYL-2-OXO-3-CYCLOPENTENE-1-CARBOXYLATE COMPOUNDS FROM 3,3-DIMETHYL-1-BUTENE-1,4-DICARBOXYLATE COMPOUNDS AND 1,3,3-TRIMETHYL-1-BUTENE-1,4-DICARBOXYLATE COMPOUNDS, AND 1,3,3-TRIMETHYL-1-BUTENE-1,4-DICARBOXYLATE COMPOUNDS

TECHNICAL FIELD

The present invention relates also to processes for preparing 5,5-dimethyl-2-oxo-3-cyclopentene-1-carboxylate compounds and 3,5,5-trimethyl-2-oxo-3-cyclopentene-1-carboxylate compounds from 3,3-dimethyl-1-butene-1,4-dicarboxylate compounds and 1,3,3-trimethyl-1-butene-1,4-dicarboxylate compounds, respectively. The present invention also relates to the 1,3,3-trimethyl-1-butene-1,4-dicarboxylate compounds.

BACKGROUND ART

A 5,5-dimethyl-2-oxo-3-cyclopentene-1-carboxylate compound and a 3,5,5-trimethyl-2-oxo-3-cyclopentene-1-carboxylate compound are useful intermediates for synthesizing biologically active substances and pheromones which have a 5-membered ring. For instance, a-necrodyl compounds, i.e., a group of compounds having a (3,4,5,5-tetramethyl-2-cyclopentenyl)methyl group, and y-necrodyl compounds, i.e., a group of compounds having a (2,2,3,4-tetramethyl-3-cyclopentenyl)methyl group, are naturally present as biologically active substances. These compounds may be derived from 3,5,5-trimethyl-2-oxo-3-cyclopentene-1-carboxylate compounds. Specifically, the 3,5,5-trimethyl-2-oxo-3-cyclopentene-1-carboxylate compounds are useful as intermediates for synthesizing (1RS,4RS)-(3,4,5,5-tetramethyl-2-cyclopentenyl)methyl isobutyrate, which is a sex pheromone of grape mealybug (scientific name: *Pseudococcus maritimus*), and (2,2,3,4-tetramethyl-3-cyclopentenyl)methyl isobutyrate, which is a sex pheromone of spherical mealybug (scientific name: *Nipaecoccus viridis*) (Non-Patent Literatures 1 and 2 listed below).

For preparing the 5,5-dimethyl-2-oxo-3-cyclopentene-1-carboxylate compound, it is reported that 4,4-dimethylcyclopent-2-ene-1-one is reacted with a base to form an enolate, which is then reacted with methyl cyanoformate to obtain methyl 5,5-dimethyl-2-oxo-3-cyclopentene-1-carboxylate (Non-Patent Literature 3 listed below).

LIST OF THE PRIOR ART

[Non-Patent Literature 1] J. G. Millar et al., J. Agric. FoodChem., 2010, 58, 4977-4982.
[Non-Patent Literature 2] A. Levi-Zada et al., J. Chem. Ecol., 2019, 45, 455-463.
[Non-Patent Literature 3] J. Richers et al., Chem. Eur. J., 2017, 23, 3178-3183.

SUMMARY OF THE INVENTION

As mentioned above, a process for preparing a 5,5-dimethyl-2-oxo-3-cyclopentene-1-carboxylate compound is known as described by Richers et al in Non-Patent Literature 3. However, methoxycarbonylation of 4,4-dimethyl-2-cyclopentene-1-one is carried out at −78° C. in Non-Patent Literature 3 and, accordingly, requires a special facility for a low-temperature reaction. In the process, desired C-methoxycarbonylation competes with undesired 0-methoxycarbonylation in the reaction of the prepared enolate with methyl cyanoformate, so that the target compound may not be obtained in a high yield. Moreover, harmful cyanide ions are formed from methyl cyanoformates in an equivalent amount, so that careful post-treatment is required. Thus, the process is unfavorable in view of safety.

The present invention has been made in these circumstances, and aims to provide a 5,5-dimethyl-2-oxo-3-cyclopentene-1-carboxylate compound and a 3,5,5-trimethyl-2-oxo-3-cyclopentene-1-carboxylate compound safely and in high yields, without using a low-temperature reaction facility.

As a result of the intensive researches, the present inventors have found that a Dieckmann condensation of a 3,3-dimethyl-1-butene-1,4-dicarboxylate compound with a base gives a 5,5-dimethyl-2-oxo-3-cyclopentene-1-carboxylate compound in a high yield, and thus have completed the present invention.

As another result of the intensive researches, the present inventors have also found that a Dieckmann condensation of a 1,3,3-trimethyl-1-butene-1,4-dicarboxylate compound with a base gives a 3,5,5-trimethyl-2-oxo-3-cyclopentene-1-carboxylate compound in a high yield, and thus have completed the present invention.

According to one aspect of the present invention, there is provided a process for preparing a compound of the following general formula (2):

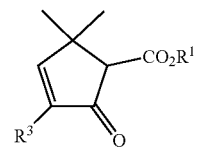

wherein $R^1$ represents a monovalent hydrocarbon group having 1 to 10 carbon atoms,
and $R^3$ represents a hydrogen atom or a methyl group,
the process comprising:
subjecting a compound of the following general formula (1):

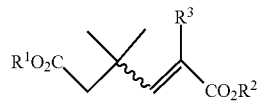

wherein $R^1$ represents a monovalent hydrocarbon group having 1 to 10 carbon atoms,
$R^2$ represents a monovalent hydrocarbon group having 1 to 10 carbon atoms, $R^3$ is as defined above and the wavy bond represents an E-configuration, a Z-configuration, or a mixture thereof,
to a Dieckmann condensation in the presence of a base to form the compound (2).

According to another aspect of the present invention, the aforesaid process for preparing the compound (2) further comprises:

subjecting a phosphonate anion generated from a phosphonate compound of the following general formula (3):

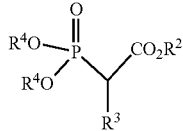

(3)

wherein $R^2$ and $R^3$ are as defined above, and $R^4$ represents a monovalent hydrocarbon or halogenated alkyl group having 1 to 10 carbon atoms,
to a Horner-Wadsworth-Emmons reaction with an aldehyde compound of the following general formula (4):

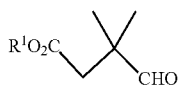

(4)

wherein $R^1$ is as defined above,
to form the compound (1).

According to another aspect of the present invention, there is further provided a 1,3,3-trimethyl-1-butene-1,4-dicarboxylate compound of the following general formula (5):

(5)

wherein $R^1$ and $R^2$ represent, independently of each other, a monovalent hydrocarbon group having 1 to 10 carbon atoms, and the wavy bond represents an E-configuration, a Z-configuration, or a mixture thereof.

The present invention provides the 3,3-dimethyl-1-butene-1,4-dicarboxylate compound and the 1,3,3-trimethyl-1-butene-1,4-dicarboxylate compound which are useful as intermediates for preparing a 5,5-dimethyl-2-oxo-3-cyclopentene-1-carboxylate compound and a 3,5,5-trimethyl-2-oxo-3-cyclopentene-1-carboxylate compound, respectively. According to the present invention, the 5,5-dimethyl-2-oxo-3-cyclopentene-1-carboxylate compound and the 3,5,5-trimethyl-2-oxo-3-cyclopentene-1-carboxylate compound are prepared in high yields without forming harmful by-products and without a low-temperature reaction facility. Surprisingly, the target compounds can be convergently produced from (E)-3,3-dimethyl-1-butene-1,4-dicarboxylate compound and (E)-1,3,3-trimethyl-1-butene-1,4-dicarboxylate compound, so that preparation of the 5,5-dimethyl-2-oxo-3-cyclopentene-1-carboxylate compound and the 3,5,5-trimethyl-2-oxo-3-cyclopentene-1-carboxylate compound are obtained in high yields.

DETAILED DESCRIPTION OF THE PREFERRED EMBODIMENTS

Embodiments of the present invention will be described in detail below. It should be understood that the present invention is not limited to or by the embodiments. The intermediates, the reagents, and the target compounds represented by the chemical formulae in the present specification may have some enantiomers. Unless otherwise stated, each chemical formula shall be interpreted to represent all possible isomers. The isomers may be used either alone or in combination thereof.

A. The 5,5-dimethyl-2-oxo-3-cyclopentene-1-carboxylate compound and the 3,5,5-trimethyl-2-oxo-3-cyclopentene-1-carboxylate compound which are prepared in the processes according to the present invention will be first described hereinafter.

The 5,5-dimethyl-2-oxo-3-cyclopentene-1-carboxylate compound and the 3,5,5-trimethyl-2-oxo-3-cyclopentene-1-carboxylate compound are comprehensively represented by the following general formula (2), and the 5,5-dimethyl-2-oxo-3-cyclopentene-1-carboxylate compound and the 3,5,5-trimethyl-2-oxo-3-cyclopentene-1-carboxylate compound may hereinafter be simply referred to as "compound (2)".

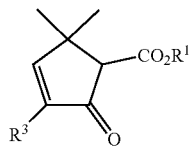

(2)

$R^1$ in the general formula (2) represents a monovalent hydrocarbon group having 1 to 10 carbon atoms, preferably 1 to 4 carbon atoms.

Examples of the monovalent hydrocarbon group of $R^1$ include linear saturated hydrocarbon groups such as a methyl group, an ethyl group, an n-propyl group, an n-butyl group, an n-pentyl group, an n-hexyl group, an n-heptyl group, an n-octyl group, an n-nonyl group, and an n-decyl group; branched saturated hydrocarbon groups such as an isopropyl group, a 2-methylbutyl group, and a t-butyl group; cyclic saturated hydrocarbon groups such as a cyclopropyl group, a cyclobutyl group, a cyclopentyl group, a cyclohexyl group, and a cyclopentylmethyl group; linear unsaturated hydrocarbon groups such as a vinyl group, an allyl group, and an ethynyl group; branched unsaturated hydrocarbon groups such as an isopropenyl group and a 2-methyl-2-propenyl group; cyclic unsaturated hydrocarbon groups such as a phenyl group, a tolyl group, a dimethylphenyl group, a benzyl group, and a phenethyl group; and isomers thereof. A part of the hydrogen atoms in the hydrocarbon groups may be substituted with a monovalent hydrocarbon group having 1 to 9 carbon atoms.

$R^3$ in the general formula (2) represents a hydrogen atom or a methyl group. When $R^3$ is a hydrogen atom, the general formula (2) represents the 5,5-dimethyl-2-oxo-3-cyclopentene-1-carboxylate compound. When $R^3$ is a methyl group, the general formula (2) represents the 3,5,5-trimethyl-2-oxo-3-cyclopentene-1-carboxylate compound.

Specific examples of the compound (2) include 5,5-dimethyl-2-oxo-3-cyclopentene-1-carboxylate compounds such as methyl 5,5-dimethyl-2-oxo-3-cyclopentene-1-carboxylate, ethyl 5,5-dimethyl-2-oxo-3-cyclopentene-1-carboxylate, t-butyl 5,5-dimethyl-2-oxo-3-cyclopentene-1-carboxylate, and phenyl 5,5-dimethyl-2-oxo-3-cyclopentene-1-carboxylate; and 3,5,5-trimethyl-2-oxo-3-cyclopentene-1-carboxylate compounds such as methyl 3,5,5-trimethyl-2-oxo-3-cyclopentene-1-carboxylate, ethyl 3,5,5-trimethyl-2-oxo-3-cyclopentene-1-carboxylate, t-butyl 3,5,5-trimethyl- 2-oxo-3-cyclopentene-1-carboxylate, and phenyl 3,5,5-trimethyl-2-oxo-3-cyclopentene-1-carboxylate.

B. Next, the process for preparing the compound (2) according to the present invention will be described hereinafter.

The present inventors have contemplated a plan for synthesis of the compound (2), as explained hereinafter.

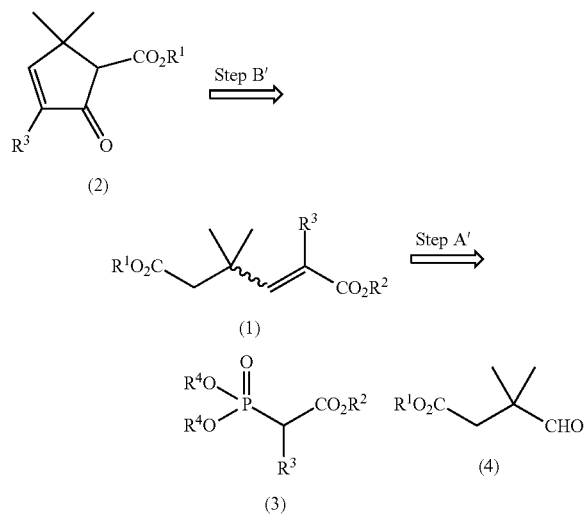

In the reaction formulae of the retrosynthetic analysis, open arrows represent transformation in the retrosynthetic analysis. Unless otherwise specifically stated herein, the wavy bond in the chemical structure represents an E-configuration, a Z-configuration, or a mixture thereof.

Step B' A target compound of the present invention, the compound (2), i.e., the 5,5-dimethyl-2-oxo-3-cyclopentene-1-carboxylate compound and the 3,5,5-trimethyl-2-oxo-3-cyclopentene-1-carboxylate compound, is thought to be synthesized by subjecting the compound (1), i.e., the 3,3-dimethyl-1-butene-1,4-dicarboxylate compound and the 1,3,3-trimethyl-1-butene-1,4-dicarboxylate compound to a Dieckmann condensation in the presence of a base. The 5,5-dimethyl-2-oxo-3-cyclopentene-1-carboxylate compound and the 3,5,5-trimethyl-2-oxo-3-cyclopentene-1-carboxylate compound are hereinafter simply referred to as "compound (1)". A preferred geometric isomer of the compound (1) is thought to be of a Z-configuration, because a Z-configuration is suitable for ring formation, that is, two carbon atoms which will be bonded in ring formation exist on the same side of the double bond.

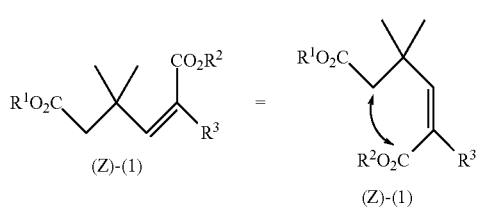

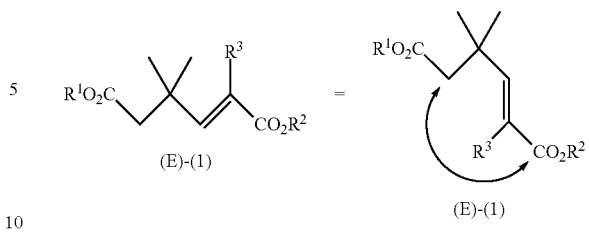

In the formulas above, an arrow indicates a position at which two carbon atoms will newly bonded.

Step A' A target compound, compound (1) is thought to be synthesized in a Horner-Wadsworth-Emmons reaction (hereinafter also referred to as "HWE reaction") between a phosphonate anion generated from a phosphonate compound of the general formula (3) shown in the reaction formula above with an aldehyde compound of the general formula (4) shown in the reaction formula above.

Taking the aforementioned retrosynthetic analysis into consideration, a reaction formula for an embodiment of the present invention is as follows.

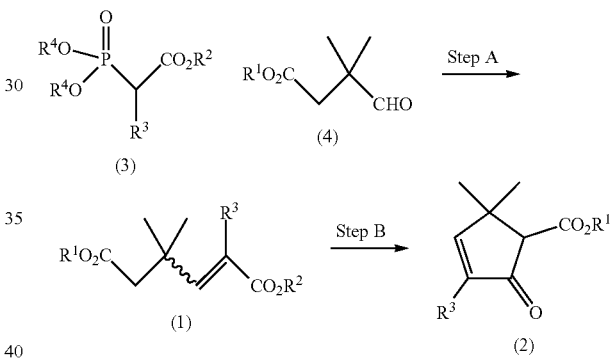

Steps A and B, which are embodiments of the present invention, will be explained in detail below.

Step B is taken up first, in which a target compound of the present invention, compound (2), is synthesized. Then, Step A is explained, in which a starting material in Step B is synthesized. In the description of Step A, a process for synthesizing a 1,3,3-trimethyl-1-butene-1,4-dicarboxylate compound of the following general formula (5), which is a compound (1) wherein $R^3$ is a methyl group, will also be described.

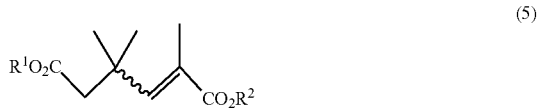

[1] Step B

Step B in which a compound (2) is synthesized will be described hereinafter. The compound (2) is synthesized by subjecting a compound (1) to a Dieckmann condensation in the presence of base, as shown in the following chemical reaction formula.

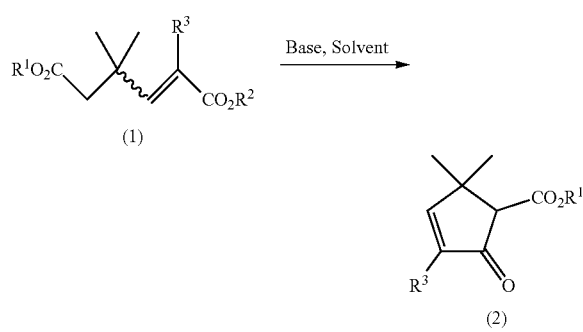

R$^1$ in the general formula (1) represents a monovalent hydrocarbon group having 1 to 10 carbon atoms. R$^2$ in the general formula (1) represents a monovalent hydrocarbon group having 1 to 10, preferably 1 to 4, carbon atoms. R$^3$ in the general formula (1) is same as R$^3$ defined in the general formula (2).

Specific examples of the compound (1) include (E)-3,3-dimethyl-1-butene-1,4-dicarboxylate compounds such as (E)-diethyl 3,3-dimethyl-1-butene-1,4-dicarboxylate, (E)-t-butyl 5-ethoxycarbonyl-4,4-dimethyl-2-pentenoate, and (E)-ethyl 4,4-dimethyl-5-phenoxycarbonyl-2-pentenoate; (Z)-3,3-dimethyl-1-butene-1,4-dicarboxylate compounds such as (Z)-diethyl 3,3-dimethyl-1-butene-1,4-dicarboxylate, (Z)-t-butyl 5-ethoxycarbonyl-4,4-dimethyl-2-pentenoate, and (Z)-ethyl 4,4-trimethyl-5-phenoxycarbonyl-2-pentenoate; (E)-1,3,3-trimethyl-1-butene-1,4-dicarboxylate compounds such as (E)-diethyl 1,3,3-trimethyl-1-butene-1,4-dicarboxylate, (E)-t-butyl 5-ethoxycarbonyl-2,4,4-trimethyl-2-pentenoate, and (E)-ethyl 2,4,4-trimethyl-5-phenoxycarbonyl-2-pentenoate; and (Z)-1,3,3-trimethyl-1-butene-1,4-dicarboxylate compounds such as (Z)-diethyl 1,3,3-trimethyl-1-butene-1,4-dicarboxylate, (Z)-t-butyl 5-ethoxycarbonyl-2,4,4-trimethyl-2-pentenoate, and (Z)-ethyl 2,4,4-trimethyl-5-phenoxycarbonyl-2-pentenoate.

1,3,3-Trimethyl-1-butene-1,4-dicarboxylate compounds of the general formula (5), which are compounds (1) wherein R$^3$ is a methyl group, such as (Z)-diethyl 1,3,3-trimethyl-1-butene-1,4-dicarboxylate and (E)-diethyl 1,3,3-trimethyl-1-butene-1,4-dicarboxylate, are preferred for the preparation of 3,5,5-trimethyl-2-oxo-3-cyclopentene-1-carboxylate compounds which are useful as intermediates for the preparation of sex pheromones of grape mealybug and spherical mealybug.

Specific examples of the 1,3,3-trimethyl-1-butene-1,4-dicarboxylate compounds (5) include (Z)-1,3,3-trimethyl-1-butene-1,4-dicarboxylate compounds of the following general formula (Z)-(5), (E)-1,3,3-trimethyl-1-butene-1,4-dicarboxylate compounds of the following general formula (E)-(5), and both.

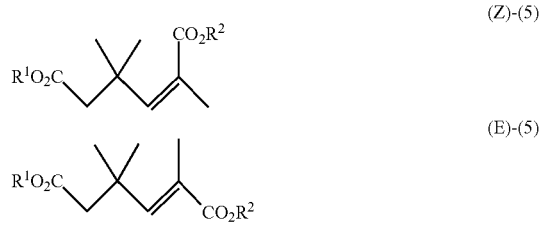

The 1,3,3-trimethyl-1-butene-1,4-dicarboxylate compounds (5) may be synthesized through a HWE reaction described below.

Compounds (2) may be synthesized by reacting compounds (1) in the presence of a base in a solvent.

Example of the base used in the preparation of compounds (2) include metal alkoxides such as sodium t-butoxide, potassium t-butoxide, sodium methoxide, potassium methoxide, sodium ethoxide, and potassium ethoxide; alkyllithium such as n-butyllithium and t-butyllithium; metal hydrides such as lithium hydride, sodium hydride, and potassium hydride; metal acetylides such as lithium acetylide and sodium acetylide; metal amides such as lithium diisopropylamide and sodium bis(trimethylsilyl)amide; and amines such as 1,8-diazabicyclo[5.4.0]-7-undecene, 1,5-diazabicyclo[4.3.0]-5-nonene, and N,N-diisopropylethylamine. Metal alkoxides such as sodium t-butoxide, potassium t-butoxide, sodium methoxide, and sodium ethoxide are preferred in view of the reactivity.

An amount of the base used is preferably from 1.0 to 5.0 mol, more preferably 1.0 to 3.0 mol, per mol of the compound (1) in view of the reactivity.

Examples of the solvent used in the preparation of compounds (2) include ether solvents such as tetrahydrofuran, 4-methyl tetrahydropyran, diethyl ether, and t-butyl methyl ether; hydrocarbon solvents such as toluene, xylene, and hexane; and polar solvents such as N,N-dimethyl formamide, N,N-dimethyl acetamide, acetonitrile, dichloromethane, and chloroform. The ether solvents such as tetrahydrofuran, and the hydrocarbon solvents such as toluene are preferred in view of the reactivity.

The solvent may be used either alone or in combination thereof, if necessary. A mixed solvent of tetrahydrofuran and toluene is preferred in view of the reactivity and solubility. The solvent may be commercially available one.

An amount of the solvent used varies, depending on a production scale, and is preferably from 200 to 4,000 g per mol of the compound (1) in view of the reaction rate.

A reaction temperature in the preparation of compounds (2) varies, depending on a solvent to be used, and is preferably from 0 to 150° C., and more preferably 30 to 80° C., in view of the reactivity and the isomerization rate.

A reaction time in the preparation of compounds (2) varies, depending on a solvent and/or a reaction scale to be used, and is preferably from 0.1 to 20 hours.

In an embodiment of the preparation of compounds (2), a 3,5,5-trimethyl-2-oxo-3-cyclopentene-1-carboxylate compound of the following general formula (6), which is a compound (2) wherein R$^3$ is a methyl group, may be synthesized by subjecting a 1,3,3-trimethyl-1-butene-1,4-dicarboxylate compound (5) (Z/E=94:6) of the following general formula (5), which is a compound (1) wherein R$^3$ is a methyl group, to a Dieckmann condensation in the presence of a base, as shown in the following chemical reaction formula. 1,3,3-Trimethyl-1-butene-1,4-dicarboxylate compounds (5) are synthesized through a Z-selective HWE reaction described below.

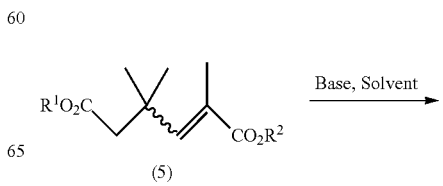

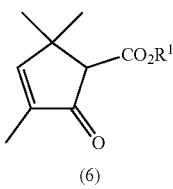

(6)

It was expected that a Dieckmann condensation would not proceed with an E-configuration, (E)-1,3,3-trimethyl-1-butene-1,4-dicarboxylate compound ((E)-(5)). Surprisingly, it has been found that the E-configuration undergoes a Dieckmann condensation to convergently provide the target compound, 3,5,5-trimethyl-2-oxo-3-cyclopentene-1-carboxylate compound (6). To validate this phenomenon, an E-configuration-rich 1,3,3-trimethyl-1-butene-1,4-dicarboxylate compound (5) (Z/E=33:67) has been subjected to the condensation reaction to find that the target compound, In the aforesaid condensation reaction, a 3,3-dimethyl-5-oxo-1-cyclopentene-1-carboxylate compound of the following general formula (11), which is not the target compound, may also formed in addition to the target compound, 5,5-dimethyl-2-oxo-3-cyclopentene-1-carboxylate compound.

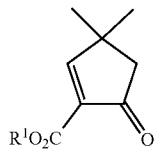

(11)

This might be because the following scheme of reactions occurs.

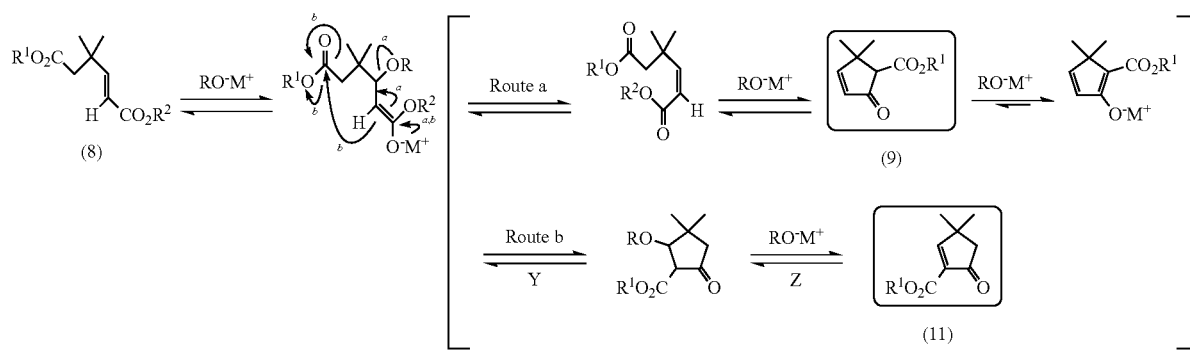

3,5,5-trimethyl-2-oxo-3-cyclopentene-1-carboxylate compound (6) is produced from an E-configuration. Thanks to this finding, it is unnecessary to carry out the HWE reaction in a Z-selective manner, and 3,5,5-trimethyl-2-oxo-3-cyclopentene-1-carboxylate compound (6) can be synthesized more efficiently.

In another embodiment of the preparation of compounds (2), a 5,5-dimethyl-2-oxo-3-cyclopentene-1-carboxylate compound of the following general formula (9), which is a compound (2) wherein $R^3$ is a hydrogen atom, may be synthesized by subjecting a 4,4-dimethyl-2-hexenedicarboxylate compound of the following general formula (8), which is a compound (1) wherein $R^3$ is a hydrogen atom, to a Dieckmann condensation in the presence of base, as shown in the following chemical reaction formula.

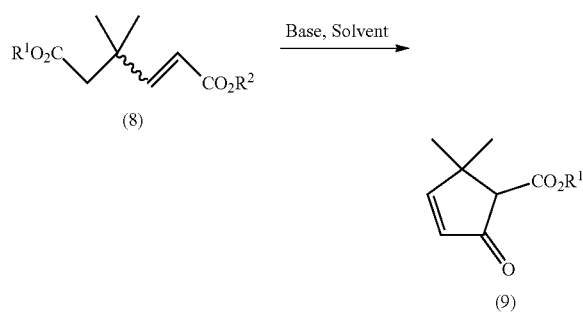

In the scheme, the rightwards harpoon over the leftwards harpoons represent a reversible equilibrium; $R^1$ and $R^2$ are as defined in compound (1); R represents an alkyl group; and $M^+$ represents a cationic moiety.

In the scheme, the base, $RO^-M^+$, attaches to and leaves from the conjugated double bond of a 3,3-dimethyl-1-butene-1,4-dicarboxylate compound (8), so that the double bond is isomerized to promote a Dieckmann condensation from the Z-configuration so as to form the target compound, 5,5-dimethyl-2-oxo-3-cyclopentene-1-carboxylate compound (9) (Route a).

Meanwhile, after the base, $RO^-M^+$, attaches to the conjugated double bond of a 3,3-dimethyl-1-butene-1,4-dicarboxylate compound (8), the carbonyl carbon atom in the resulting enolate is attacked to form a cyclopentanone compound (Route b); and the OR group in this cyclopentanone compound is eliminated to form a 3,3-dimethyl-5-oxo-1-cyclopentene-1-carboxylate compound (11), which is not the target compound.

As mentioned above, when Win the general formula (1) is a hydrogen atom (i.e., the case of the 3,3-dimethyl-1-butene-1,4-dicarboxylate compound (8)), the side reactions, Route b, occur besides the envisaged reactions in Route a.

On the other hand, when Win the general formula (1) is a methyl group (i.e., the case of 1,3,3-trimethyl-1-butene-1,4-dicarboxylate compound (5)), the resulting cyclopentanone compound has no hydrogen atom on the carbon atom between sandwiched by the keto group and the ester group, so that the OR group does not leave and no equilibrium occur, unlike the equilibrium Z shown in the aforementioned scheme. According to the aforesaid surmised theory, the Route a occurs mainly to provide its product.

Therefore, the processes according to the present invention are particularly suitable to apply to a compound of the general formula (1) wherein $R^3$ is a methyl group (i.e., 1,3,3-trimethyl-1-butene-1,4-dicarboxylate compound (5)). When a 3,3-dimethyl-1-butene-1,4-dicarboxylate compound (8) comprises its E-configuration in a larger proportion, the undesired 3,3-dimethyl-5-oxo-1-cyclopentene-1-carboxylate compound (11) occurs in a larger proportion, and vise versa. Accordingly, when $R^3$ in the general formula (1) is a hydrogen atom, it is preferred to use a Z-configuration-rich 3,3-dimethyl-1-butene-1,4-dicarboxylate compound (8).

[2] Step A

Next, Step A will be described, in which compound (1) is synthesized. A compound (1) is obtained by a HWE reaction between a phosphonate anion derived from a phosphonate compound (3) and an aldehyde compound (4), as shown in the following chemical reaction formula.

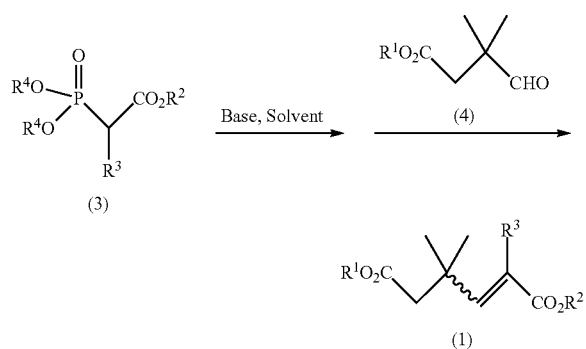

$R^2$ in the general formula (3) is as defined in the general formula (1).

$R^3$ in the general formula (3) is as defined in the general formula (2). $R^4$ in the general formula (3) represents a monovalent hydrocarbon or halogenated alkyl group having 1 to 10, preferably 1 to 6, carbon atoms.

Examples of the monovalent hydrocarbon group of $R^4$ include linear saturated hydrocarbon groups such as a methyl group, an ethyl group, an n-propyl group, an n-butyl group, an n-pentyl group, an n-hexyl group, an n-heptyl group, an n-octyl group, an n-nonyl group, and an n-decyl group; branched saturated hydrocarbon groups such as an isopropyl group, a 2-methylbutyl group, and a t-butyl group; cyclic saturated hydrocarbon groups such as a cyclopropyl group, a cyclobutyl group, a cyclopentyl group, a cyclohexyl group, and a cyclopentylmethyl group; linear unsaturated hydrocarbon groups such as a vinyl group, an allyl group, and an ethynyl group; branched unsaturated hydrocarbon groups such as an isopropenyl group and a 2-methyl-2-propenyl group; cyclic unsaturated hydrocarbon groups such as a phenyl group, a tolyl group, a dimethylphenyl group, a benzyl group, and a phenethyl group; and isomers thereof. A part of the hydrogen atoms in the hydrocarbon groups may be substituted with a monovalent hydrocarbon group having 1 to 9 carbon atoms.

Examples of the monovalent halogenated alkyl group of $R^4$ include halogenated alkyl groups such as a trifluoroethyl group, which is used in Still-Gennari method and other methods which enables a Z-selective HWE reaction.

Examples of the phosphonate compound (3) include 2-phosphonopropionate compounds such as triethyl 2-phosphonopropionate and ethyl 2-(diphenylphosphono) propionate; phosphonoacetate compounds such as triethyl phosphonoacetate and ethyl diphenylphosphonoacetate; and phosphonate compounds used in a Still-Gennari method, such as bis(2,2,2-trifluoroethyl)(methoxycarbonylmethyl) phosphonate.

The phosphonate compound (3) may be commercially available one or may be synthesized in house. For example, the compound may be synthesized by subjecting a halogenated alkyl and a phosphite ester to an Arbuzov reaction.

$R^1$ in the aldehyde compound (4) is same as $R^1$ defined in the general formula (1).

Examples of the aldehyde compound (4) include 3,3-dimethyl-4-oxobutyrate compounds such as methyl 3,3-dimethyl-4-oxobutyrate, ethyl 3,3-dimethyl-4-oxobutyrate, t-butyl 3,3-dimethyl-4-oxobutyrate, and phenyl 3,3-dimethyl-4-oxobutyrate.

The aldehyde compound (4) may be commercially available one or may be synthesized in house. The compound may be synthesized in any known process or by reacting an enamine derived from an isobutyraldehyde with a haloacetate ester.

The compound (1) may be synthesized by reacting a phosphonate compound (3) in the presence of a base in a solvent to form a phosphonate anion, which is subjected to a Horner-Wadsworth-Emmons reaction with an aldehyde compound (4).

Examples of the base used in the formation of the phosphonate anion include metal alkoxides such as sodium t-butoxide, potassium t-butoxide, sodium methoxide, potassium methoxide, sodium ethoxide, and potassium ethoxide; alkyllithium such as n-butyllithium and t-butyllithium; metal hydrides such as lithium hydride, sodium hydride, and potassium hydride; metal acetylides such as lithium acetylide and sodium acetylide; metal amides such as lithium diisopropylamide and sodium bis(trimethylsilyl)amide; and amines such as 1,8-diazabicyclo[5.4.0]-7-undecene, 1,5-diazabicyclo[4.3.0]-5-nonene, and N,N-diisopropylethylamine. Metal hydrides such as sodium hydride, and metal acetylides such as lithium acetylide and sodium acetylide are preferred in view of the suppression of by-product formation.

The base may be used either alone or in combination thereof, if necessary. The base may be commercially available one.

An amount of the base used is preferably from 0.8 to 1.3 mol per mol of the phosphonate compound (3) in view of the reactivity and suppression of by-product formation.

Alkali metal halides such as lithium chloride and sodium iodide may be added in the preparation of phosphonate anions, if necessary.

An amount of the alkali metal halide used is preferably 0.01 to 1.3 mol per mol of the phosphonate compound (3) in view of the reactivity and costs.

Examples of the solvent in the formation of phosphonate anions include ether solvents such as tetrahydrofuran, 4-methyl tetrahydropyran, diethyl ether, and t-butyl methyl ether; hydrocarbon solvents such as toluene, xylene, and hexane; and polar solvents such as N,N-dimethyl formamide, N,N-dimethyl acetamide, acetonitrile, dichloromethane, and chloroform. Tetrahydrofuran, acetonitrile, N,N-dimethyl formamide, and N,N-dimethyl acetamide, which are widely used in the HWE reactions, are particularly preferred. Hydrocarbon solvents are also preferred because sodium acetylide used as the base is dissolved in xylene.

The solvent may be used either alone or in combination thereof, if necessary. A mixed solvent of tetrahydrofuran and xylene is preferred in view of the reactivity and solubility. The solvent may be commercially available one.

An amount of the solvent used varies, depending on a production scale, and is preferably from 200 to 4,000 g per mol of the phosphonate compound (3) in view of the reaction rate.

A reaction temperature in the formation of phosphonate anions varies, depending on a solvent to be used, and is preferably from −78 to 150° C., and more preferably 0 to 80° C., in view of the reactivity and suppression of by-product formation.

A reaction time of the formation of phosphonate anions varies, depending on a solvent and/or a reaction scale to be used, and is preferably from 0.1 to 20 hours.

An amount of the aldehyde compound (4) used in the HWE reaction is preferably from 0.7 to 1.3 mol per mol of the phosphonate compound (3) in view of the reactivity and costs.

Solvent and an amount of the solvent used in the HWE reaction may be same as or different from those in the formation of phosphonate anions.

A reaction temperature in the HWE reaction varies, depending on a solvent to be used, and is preferably from −78 to 150° C., and more preferably 0 to 80° C., in view of the reactivity and suppression of by-product formation.

A reaction time of the HWE reaction varies, depending on a solvent and/or a reaction scale to be used, and is preferably from 0.1 to 20 hours.

If it is difficult to purify the product of the HWE reaction due to similarity in polarity or a boiling point between the product and the starting phosphonate compound (3) or aldehyde compound (4), another or other phosphonate compounds and/or another or other aldehyde compounds which is/are different from those used in the reaction may be added after the reaction to consume the excessive starting material.

Examples of the another or other phosphonate compounds used to consume the excessive starting material include phosphonoacetates such as triethyl 2-phosphonopropionate and triethyl phosphonoacetate. Examples of the another or other aldehyde compounds used to consume the excessive starting material include lower aldehydes such as formaldehyde, acetaldehyde, propionylaldehyde, butyraldehyde, and isobutyraldehyde; and higher aldehydes such as decanal, undecanal, and dodecanal.

Amounts of the another or other phosphonate compounds and another or other aldehyde compounds used are preferably from 0.01 to 0.5 mol per mol of the phosphonate compound (3) in view of the reactivity and costs.

A specific example of the Z-selective HWE reaction is a case where $R^2$ is an ethyl group, $R^3$ is a methyl group, and $R^4$ is a phenyl group in the general formula (3), and $R^1$ is an ethyl group in the general formula (4), as shown in the following chemical reaction formula.

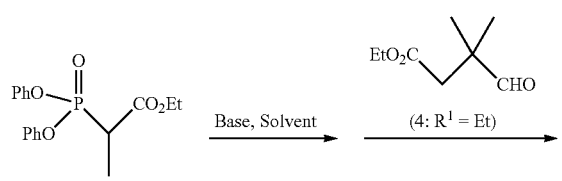

(3: $R^2$ = Et; $R^3$ = Me; $R^4$ = Ph)

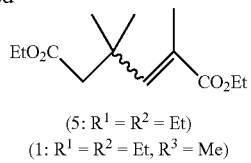

-continued (5: $R^1$ = $R^2$ = Et)
(1: $R^1$ = $R^2$ = Et, $R^3$ = Me)

A specific example of the HWE reaction which produces a mixture of a Z-configuration and an E-configuration is a case where $R^2$ and $R^4$ are an ethyl group and $R^3$ is a methyl group in the general formula (3), and $R^1$ is an ethyl group in the general formula (4), as shown in the following chemical reaction formula.

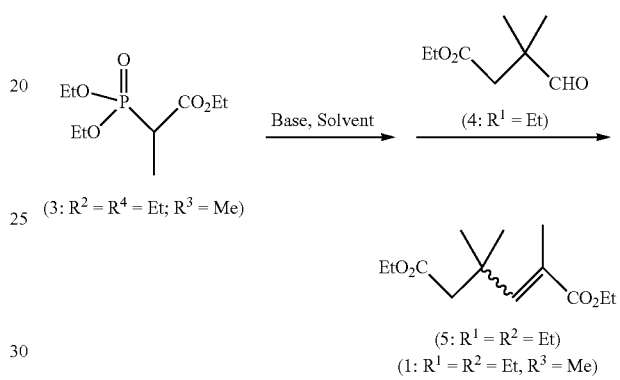

(3: $R^2$ = $R^4$ = Et; $R^3$ = Me)

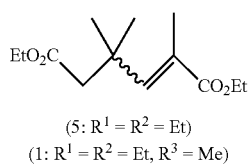

(5: $R^1$ = $R^2$ = Et)
(1: $R^1$ = $R^2$ = Et, $R^3$ = Me)

A 1,3,3-trimethyl-1-butene-1,4-dicarboxylate compound (5), which is a compound (1) useful for preparing 3,5,5-trimethyl-2-oxo-3-cyclopentene-1-carboxylate compounds, may be synthesized, for example, by a HWE reaction between a phosphonate anion formed from a 2-phosphonopropionate compound and a 3,3-dimethyl-4-oxobutyrate compound.

Thus, there are provided processes for preparing 3,3-dimethyl-1-butene-1,4-dicarboxylate and 1,3,3-trimethyl-1-butene-1,4-dicarboxylate compounds, which are useful intermediates for syntheses, 5,5-dimethyl-2-oxo-3-cyclopentene-1-carboxylate compounds and 3,5,5-trimethyl-2-oxo-3-cyclopentene-1-carboxylate compounds, each in a high yield.

EXAMPLES

The present invention will be described with reference to the following Examples. It should be construed that the present invention is not limited to or by the Examples.

The term "purity" as used herein means an area percentage determined by gas chromatography (hereinafter also referred to as "GC"), unless otherwise specified. The term "production ratio" means a relative ratio of area percentages determined by GC.

A yield is calculated from the area percentages determined by GC.

The yield was calculated by the following equation in consideration of purities (% GC) of a starting material and a product.

Yield (%)=[(mass of a product obtained in a reaction x % GC)/molecular mass of a product]÷[(mass of a starting material x % GC)/ molecular mass of a starting material]}×100

The term "crude yield" refers to a yield of a crude product obtained without purification.

In the Examples, monitoring of the reactions and calculation of the yields were carried out in the following GC conditions.

GC conditions: GC: Capillary gas chromatograph GC-2014 (Shimadzu Corporation); column: DB-5, 0.25 um×0.25 mmϕ×30 m; carrier gas: He (1.55 mL/min), detector: FID; column temperature: 100° C., elevated by 10° C./min, up to 230° C.

Example 1: Preparation of Diethyl 1,3,3-trimethyl-1-butene-1,4-dicarboxylate (5: $R^1=R^2=Et$; 1: $R^1=R^2=Et$, $R^3=Me$)

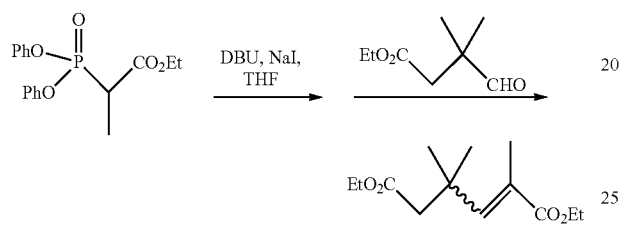

wherein Ph represents a phenyl group, and Et represents an ethyl group.

Ethyl 2-(diphenoxyphosphinyl)propanoate (139 g, 0.415 mol) (3: $R^2=Et$; $R^3=Me$; $R^4=Ph$) and tetrahydrofuran (THF) (1,452 g) were placed in a reactor and cooled to 4 to 6° C. while stirring. Sodium iodide (NaI) (99.5 g, 0.664 mol) was then added, and 1,8-diazabicyclo[5.4.0]-7-undecene (DBU) (94.8 g, 0.622 mol) was subsequently added dropwise at 4 to 9° C. After the completion of the dropwise addition, the mixture was stirred at 4 to 9° C. for 30 minutes, to which ethyl 3,3-dimethyl-4-oxobutyrate (4: $R^1=Et$) (140 g, 0.887 mol) was then added dropwise at 4 to 9° C. After the completion of the dropwise addition, the mixture was stirred at 57 to 62° C. for 8 hours and cooled to 4 to 6° C. An aqueous solution of ammonium chloride (804 g: prepared from ammonium chloride (78 g) and water (726 g)) was added to quench the reaction, and ethyl acetate (871 g) was subsequently added. The resulting reaction mixture was phase-separated. The resulting organic layer was then washed with brine (1,260 g: prepared from sodium chloride (60 g) and water (1,200 g)). The organic layer was concentrated at a reduced pressure, and the concentrate was distilled at a reduced pressure to obtain diethyl 1,3,3-trimethyl-1-butene-1,4-dicarboxylate (5: $R^1=R^2=Et$) (70.5 g, 0.291 mol; Z/E=94:6) in 70.2% yield.

The following are spectrum data of (Z)-diethyl 1,3,3-trimethyl-1-butene-1,4-dicarboxylate (5: $R^1=R^2=Et$) thus prepared.

Nuclear magnetic resonance spectrum: $^1$H-NMR (500 MHz, CDCl$_3$): δ 1.19 (s, 6H), 1.23 (t, J=7.3 Hz, 3H), 1.30 (t, J=7.3 Hz, 3H), 1.90 (d, J=1.5 Hz, 3H), 2.46 (s, 2H), 4.10 (q, J=7.3 Hz, 2H), 4.19 (q, J=7.3 Hz, 2H), 5.62 (q, J=1.5 Hz, 1H); $^{13}$C-NMR (75.6 MHz, CDCl$_3$): δ 14.07, 14.24, 22.58, 27.73 (2C), 35.37, 47.02, 59.98, 60.52, 127.43, 141.39, 170.33, 171.74.

Mass spectrum: EI-mass spectrum (70 eV): m/z 242 (M$^+$), 227, 196, 181, 168, 155, 139, 127, 109, 95, 81, 67, 55, 41, 29.

Infrared absorption spectrum (NaCl): νmax 2980, 1731, 1452, 1369, 1342, 1322, 1246, 1204, 1100, 1036, 919, 866, 775.

The following are spectrum data of (E)-diethyl 1,3,3-trimethyl-1-butene-1,4-dicarboxylate thus prepared.

Nuclear magnetic resonance spectrum: $^1$H-NMR (500 MHz, CDCl$_3$): δ 1.21 (t, J=7.3 Hz, 3H), 1.27 (t, J=7.3 Hz, 3H), 1.28 (s, 6H), 1.94 (d, J=1.5 Hz, 3H), 2.45 (s, 2H), 4.09 (q, J=7.3 Hz, 2H), 4.16 (q, J=7.3 Hz, 2H), 6.83 (q, J=1.5 Hz, 1H); $^{13}$C-NMR (75.6 MHz, CDCl$_3$): δ 13.44, 14.21 (2C), 27.93 (2C), 35.26, 46.93, 60.11, 60.62, 127.42, 148.29, 168.88, 171.27.

Mass spectrum: EI-mass spectrum (70 eV): m/z 242 (M$^+$), 227, 196, 181, 168, 155, 139, 127, 109, 95, 81, 67, 55, 41, 29.

Infrared absorption spectrum (NaCl): νmax 2980, 1731, 1452, 1369, 1342, 1322, 1246, 1204, 1100, 1036, 919, 866, 775.

Example 2: Preparation of Diethyl 1,3,3-trimethyl-1-butene-1,4-dicarboxylate (5: $R^1=R^2=Et$; 1: $R^1=R^2=Et$, $R^3=Me$)

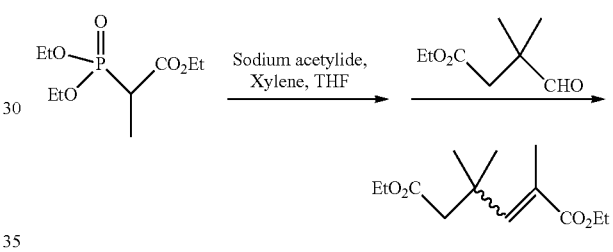

wherein Et represents an ethyl group.

A 0.00476 mol/g solution of sodium acetylide in xylene (214 g, 1.02 mol), and THF (1,325 g) were placed in a reactor and cooled to 4 to 6° C. while stirring. Triethyl 2-phosphonopropionate (3: $R^2=R^4=Et$; $R^3=Me$) (242 g, 1.02 mol) was then added dropwise at 4 to 9° C. After the completion of the dropwise addition, the mixture was heated to 62 to 67° C. Subsequently, ethyl 3,3-dimethyl-4-oxobutyrate (4: $R^1=Et$) (140 g, 0.887 mol) was added dropwise at 62 to 67° C. After the completion of the dropwise addition, the mixture was stirred at 62 to 67° C. for 1.5 hours. The mixture was then cooled to 37 to 42° C., to which isobutyraldehyde (25.5 g, 0.353 mol), sodium iodide (66.2 g, 0.441 mol), and 1,8-diazabicyclo[5.4.0]-7-undecene (53.8 g, 0.353 mol) were sequentially added and stirred at 37 to 42° C. for 1.5 hours. The mixture was then cooled to 4 to 6° C., and an aqueous solution of ammonium chloride (939 g: prepared from ammonium chloride (85 g) and water (854 g)) was added to quench the reaction. Hexane (887 g) was subsequently added. The resulting reaction mixture was phase-separated. The resulting organic layer was then washed with an aqueous solution of ammonium chloride (1,450 g: prepared from ammonium chloride (85 g), sodium chloride (33 g), and water (1,332 g), then with brine (1,399 g: prepared from sodium chloride (67 g) and water (1,332 g)). The organic layer was concentrated at a reduced pressure, and the concentrate was distilled at a reduced pressure to obtain diethyl 1,3,3-trimethyl-1-butene-1,4-dicarboxylate (5: $R^1=R^2=Et$) (177 g, 0.731 mol; Z/E=39:61) in 82.4% yield.

The various spectrum data of diethyl 1,3,3-trimethyl-1-butene-1,4-dicarboxylate (5: $R^1=R^2=Et$) thus prepared were same as those obtained in Example 1.

Example 3: Preparation of Diethyl 3,3-dimethyl-1-butene-1,4-dicarboxylate (8: $R^1=R^2=Et$; 1: $R^1=R^2=Et$, $R^3=H$)

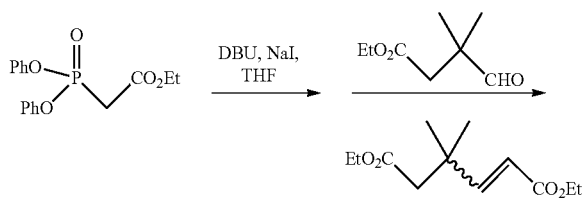

wherein Ph and Et are as defined above.

Ethyl diphenylphosphonoacetate (3: $R^2=Et$; $R^3=H$; $R^4=Ph$) (52.1 g, 0.163 mol) and THF (455 g) were placed in a reactor and cooled to 4 to 6° C. while stirring. Sodium iodide (39.0 g, 0.260 mol) was then added, and subsequently 1,8-diazabicyclo[5.4.0]-7-undecene (37.1 g, 0.244 mol) was added dropwise at 4 to 9° C. After the completion of the dropwise addition, the mixture was stirred at 4 to 9° C. for 30 minutes, and then ethyl 3,3-dimethyl-4-oxobutyrate (4: $R^1=Et$) (28.3 g, 0.179 mol) was added dropwise at 4 to 9° C. After the completion of the dropwise addition, the mixture was stirred at room temperature for 4 hours and cooled to 4 to 6° C. An aqueous solution of ammonium chloride (358 g: prepared from ammonium chloride (31 g) and water (327 g)) was then added to quench the reaction, and hexane (365 g) was then added. The resulting reaction mixture was phase-separated, and the resulting organic layer was then washed with brine (414 g: prepared from sodium chloride (20 g) and water (394 g)). The organic layer was concentrated at a reduced pressure, and the concentrate was distilled at a reduced pressure to obtain diethyl 3,3-dimethyl-1-butene-1,4-dicarboxylate (8: $R^1=R^2=Et$) (31.9 g, 0.140 mol; Z/E=78:22) in 86.0% yield.

The following are spectrum data of (Z)-diethyl 3,3-dimethyl-1-butene-1,4-dicarboxylate (8: $R^1=R^2=Et$) thus prepared.

Nuclear magnetic resonance spectrum: $^1$H-NMR (500 MHz, CDCl$_3$): δ 1.23 (t, J=7.3 Hz, 3H), 1.28 (t, J=7.3 Hz, 3H), 1.30 (s, 6H), 2.72 (s, 2H), 4.09 (q, J=7.3 Hz, 2H), 4.15 (q, J=7.3 Hz, 2H), 5.71 (d, J=13.0 Hz, 1H), 6.16 (d, J=13.0 Hz, 1H); $^{13}$C-NMR (75.6 MHz, CDCl$_3$): δ 14.13, 14.21, 27.89 (2C), 35.60, 46.01, 60.00, 60.16, 119.41, 154.29, 166.23, 171.97.

Mass spectrum: EI-mass spectrum (70 eV): m/z 228 (M$^+$), 213, 199, 183, 167, 154, 141, 126, 109, 95, 81, 67, 55, 41, 29.

Infrared absorption spectrum (NaCl): νmax 2980, 2875, 1731, 1650, 1466, 1368, 1305, 1178, 1035, 982, 864, 722.

The following are spectrum data of (E)-diethyl 3,3-dimethyl-1-butene-1,4-dicarboxylate thus prepared.

Nuclear magnetic resonance spectrum: $^1$H-NMR (500 MHz, CDCl$_3$): δ 1.18 (s, 6H), 1.23 (t, J=7.3 Hz, 3H), 1.28 (t, J=7.3 Hz, 3H), 2.35 (s, 2H), 4.10 (q, J=7.3 Hz, 2H), 4.18 (q, J=7.3 Hz, 2H), 5.76 (d, J=16.1 Hz, 1H), 7.00 (d, J=16.1 Hz, 1H); $^{13}$C-NMR (75.6 MHz, CDCl$_3$): δ 14.19, 14.21, 26.53 (2C), 35.99, 46.17, 60.23, 60.29, 118.11, 156.06, 166.89, 170.95.

Mass spectrum: EI-mass spectrum (70 eV): m/z 228 (M$^+$), 213, 199, 183, 167, 154, 141, 126, 109, 95, 81, 67, 55, 41, 29.

Infrared absorption spectrum (NaCl): νmax 2980, 2875, 1731, 1650, 1466, 1368, 1305, 1178, 1035, 982, 864, 722.

Example 4: Preparation of (E)-t-butyl 5-ethoxycarbonyl-4,4-dimethyl-2-pentenoate (8: $R^1=Et$, $R^2=^tBu$; 1: $R^1=Et$, $R^2=^tBu$, $R^3=H$)

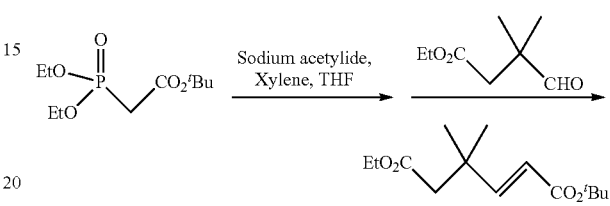

wherein $^tBu$ represents a t-butyl group, and Et represents an ethyl group.

A 0.00476 mol/g solution of sodium acetylide in xylene (43.5 g, 0.207 mol), and THF (270 g) were placed in a reactor and cooled to 4 to 6° C. while stirring. t-Butyl diethylphosphonoacetate (3: $R^2=^tBu$; $R^3=H$; $R^4=Et$) (46.4 g, 0.207 mol) was then added dropwise at 4 to 9° C. After the completion of the dropwise addition, the mixture was heated to 62 to 67° C., and then ethyl 3,3-dimethyl-4-oxobutyrate (4: $R^1=Et$) (28.5 g, 0.180 mol) was added dropwise at 62 to 67° C. After the completion of the dropwise addition, the mixture was stirred at 62 to 67° C. for 5 hours. The mixture was then cooled to 4 to 6° C., and an aqueous solution of ammonium chloride (190 g: prepared from ammonium chloride (17 g) and water (173 g)) was added to quench the reaction, and hexane (202 g) was then added. The resulting reaction mixture was phase-separated. The resulting organic layer was washed with an aqueous solution of ammonium chloride (294 g: prepared from ammonium chloride (17 g), sodium chloride (7 g), and water (270 g)), and with brine (284 g: prepared from sodium chloride (14 g) and water (270 g)). The organic layer was concentrated at a reduced pressure, and the concentrate was distilled at a reduced pressure to obtain (E)-t-butyl 5-ethoxycarbonyl-4,4-dimethyl-2-pentenoate (8: $R^1=Et$; $R^2=^tBu$) (29.4 g, 0.115 mol) in 63.7% yield.

The following are spectrum data of (E)-t-butyl 5-ethoxycarbonyl-4,4-dimethyl-2-pentenoate (8: $R^1=Et$; $R^2=^tBu$) thus prepared.

Nuclear magnetic resonance spectrum: $^1$H-NMR (500 MHz, CDCl$_3$): δ 1.16 (s, 6H), 1.21 (t, J=7.3 Hz, 3H), 1.46 (s, 9H), 2.32 (s, 2H), 4.08 (q, J=7.3 Hz, 2H), 5.66 (d, J=15.7 Hz, 1H), 6.87 (d, J=15.7 Hz, 1H); $^{13}$C-NMR (75.6 MHz, CDCl$_3$): δ 14.17, 26.55 (2C), 28.09 (3C), 35.83, 46.17, 60.14, 80.14, 119.72, 154.82, 166.19, 170.97.

Mass spectrum: EI-mass spectrum (70 eV): m/z 256 (M$^+$), 200, 183, 169, 154, 137, 113, 95, 81, 57, 41, 27.

Infrared absorption spectrum (NaCl): νmax 2977, 1734, 1715, 1651, 1466, 1392, 1368, 1318, 1152, 1036, 977, 865, 768, 723.

Example 5: Preparation of Ethyl 3,5,5-trimethyl-2-oxo-3-cyclopentene-1-carboxylate (6: $R^1$=Et; 2: $R^1$=Et, $R^3$=Me)

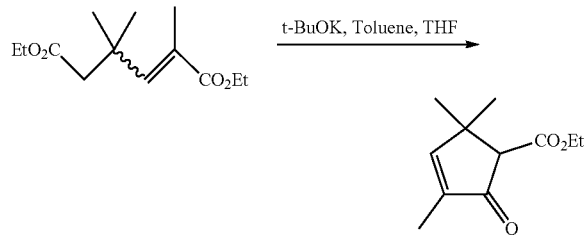

wherein Et represents an ethyl group.

Potassium t-butoxide (231 g, 2.00 mol), toluene (1,000 g), and THF (500 g) were placed in a reactor and stirred at room temperature for 20 minutes. Next, diethyl 1,3,3-trimethyl-1-butene-1,4-dicarboxylate (5: $R^1$=$R^2$=Et) obtained according to the procedures described in Example 2 (242 g, 1.00 mol; Z/E=33:67) was added dropwise at or below 40° C. After the completion of the dropwise addition, the mixture was stirred at 65 to 70° C. for 2 hours and cooled to 4 to 10° C. Then, 3.34% by weight of hydrochloric acid (2,296 g) was added to quench the reaction, and the resulting reaction mixture was then phase-separated. The resulting organic layer was then washed with water (2,000 g) twice, and with brine (2,200 g: prepared from sodium chloride (200 g) and water (2,000 g)). The resulting organic layer was concentrated at a reduced pressure, and the concentrate was distilled at a reduced pressure to obtain ethyl 3,5,5-trimethyl-2-oxo-3-cyclopentene-1-carboxylate (6: $R^1$=Et) (171 g, 0.871 mol) in 87.1% yield.

The following are spectrum data of ethyl 3,5,5-trimethyl-2-oxo-3-cyclopentene-1-carboxylate (6: $R^1$=Et) thus prepared.

Nuclear magnetic resonance spectrum: $^1$H-NMR (500 MHz, CDCl$_3$): δ 1.15 (s, 3H), 1.27 (t, J=7.3 Hz, 3H), 1.31 (s, 3H), 1.76 (d, J=1.6 Hz, 3H), 3.14 (s, 1H), 4.19 (q, J=7.3 Hz, 2H), 7.04 (q, J=1.6 Hz, 1H); $^{13}$C-NMR (75.6 MHz, CDCl$_3$): δ 9.86, 14.22, 23.90, 29.15, 42.44, 60.93, 62.67, 138.34, 166.33, 169.22, 203.61.

Mass spectrum: EI-mass spectrum (70 eV): m/z 196 (M$^+$), 181, 168, 151, 135, 123, 109, 95, 79, 67, 55, 39, 29.

Infrared absorption spectrum (NaCl): νmax 2965, 2928, 2872, 1741, 1708, 1644, 1563, 1465, 1447, 1367, 1312, 1149, 1030, 997, 953, 898, 641, 529.

Example 6: Preparation of Ethyl 5,5-dimethyl-2-oxo-3-cyclopentene-1-carboxylate (9: $R^1$=Et; 2: $R^1$=Et, $R^3$=H)

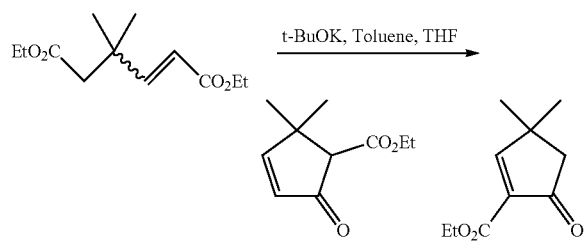

wherein Et represents an ethyl group.

Potassium t-butoxide (18.2 g, 0.162 mol), toluene (80.9 g), and THF (40.5 g) were placed in a reactor and stirred at room temperature for 10 minutes. Next, diethyl 3,3-dimethyl-1-butene-1,4-dicarboxylate (8: $R^1$=$R^2$=Et) (18.5 g, 0.0809 mol; Z/E=81:19) obtained by further distilling a portion of diethyl 3,3-dimethyl-1-butene-1,4-dicarboxylate obtained according to the procedures described in Example 3 was added dropwise at or below 35° C. After the completion of the dropwise addition, the mixture was stirred at room temperature for 30 minutes and cooled to 4 to 10° C. Then, 3.34% by weight of hydrochloric acid (186 g) was added to quench the reaction, and the resulting reaction mixture was phase-separated. The organic layer was washed with water (150 g) twice, and with saturated brine (150 mL). The resulting organic layer was concentrated at a reduced pressure. The concentrate was purified by silica gel column chromatography (eluent: a gradient of n-hexane: ethyl acetate=20:1 to 4:1) to obtain the target compound, ethyl 5,5-dimethyl-2-oxo-3-cyclopentene-1-carboxylate (9: $R^1$=Et) (10.4 g, 0.0573 mol) in 70.8% yield, and a side product, ethyl 3,3-dimethyl-5-oxo-1-cyclopentene-1-carboxylate (11: $R^1$=Et) (1.27 g, 0.00698 mol) in 8.6% yield.

The following are spectrum data of ethyl 5,5-dimethyl-2-oxo-3-cyclopentene-1-carboxylate (9: $R^1$=Et) thus prepared.

Nuclear magnetic resonance spectrum: $^1$H-NMR (500 MHz, CDCl$_3$): δ 1.19 (s, 3H), 1.26 (t, J=7.3 Hz, 3H), 1.35 (s, 3H), 3.12 (s, 1H), 4.19 (q, J=7.3 Hz, 2H), 6.05 (d, J=5.8 Hz, 1H), 7.43 (d, J=5.8 Hz, 1H); $^{13}$C-NMR (75.6 MHz, CDCl$_3$): δ 14.17, 23.59, 28.86, 45.03, 61.04, 62.48, 130.37, 168.89, 172.50, 203.65.

In the NMR spectrum, the peak corresponding to the enol form, which is a keto-enol tautomer, of ethyl 5,5-dimethyl-2-oxo-3-cyclopentene-1-carboxylate was observed in part. This spectrum is for a keto form of ethyl 5,5-dimethyl-2-oxo-3-cyclopentene-1-carboxylate, but some peaks for an enol form (i.e., keto-enol tautomer) are also seen.

Mass spectrum: EI-mass spectrum (70 eV): m/z 182 (M$^+$), 167, 154, 137, 121, 109, 95, 81, 65, 53, 39, 29.

Infrared absorption spectrum (NaCl): νmax 3400, 2968, 2938, 2874, 1742, 1707, 1594, 1469, 1368, 1316, 1252, 1229, 1145, 1036, 917, 814, 754, 694, 517.

Some absorptions by the enol form of ethyl 5,5-dimethyl-2-oxo-3-cyclopentene-1-carboxylate are also seen in the infrared absorption spectrum.

The following are spectrum data of ethyl 3,3-dimethyl-5-oxo-1-cyclopentene-1-carboxylate (11: $R^1$=Et) thus prepared.

Nuclear magnetic resonance spectrum: $^1$H-NMR (500 MHz, CDCl$_3$): δ 1.26 (s, 6H), 1.32 (t, J=7.3 Hz, 3H), 2.39 (s, 2H), 4.27 (q, J=7.3 Hz, 2H), 8.08 (s, 1H); $^{13}$C-NMR (75.6 MHz, CDCl$_3$): δ 14.12, 27.42 (2C), 38.82, 51.12, 60.94, 134.03, 161.87, 179.68, 202.47.

Mass spectrum: EI-mass spectrum (70 eV): m/z 182 (M$^+$), 167, 154, 136, 121, 110, 95, 80, 69, 53, 41, 29.

Infrared absorption spectrum (NaCl): νmax 2963, 2871, 1751, 1722, 1621, 1466, 1411, 1368, 1333, 1301, 1232, 1214, 1192, 1034, 928, 767, 725, 592.

The invention claimed is:

1. A process for preparing a compound of the following general formula (2):

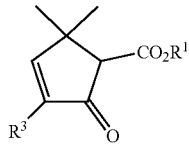

(2)

wherein $R^1$ represents a monovalent hydrocarbon group having 1 to 10 carbon atoms, and $R^3$ represents a hydrogen atom or a methyl group,
the process comprising:
subjecting a compound of the following general formula (1):

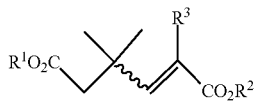

(1)

wherein $R^1$ represents a monovalent hydrocarbon group having 1 to 10 carbon atoms, $R^2$ represents a monovalent hydrocarbon group having 1 to 10 carbon atoms, $R^3$ is as defined above, and the wavy bond represents an E-configuration, a Z-configuration, or a mixture thereof,
to a Dieckmann condensation in the presence of a base to form the compound (2).

2. The process for preparing the compound (2) according to claim 1, wherein $R^1$ and $R^2$ represent an ethyl group, and $R^3$ represents a methyl group in the general formula (1).

3. The process for preparing the compound (2) according to claim 1, the process further comprising:
subjecting a phosphonate anion generated from a phosphonate compound of the following general formula (3):

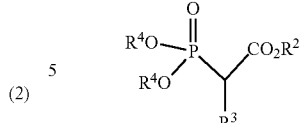

(3)

wherein $R^2$ and $R^3$ are as defined above, and $R^4$ represents a monovalent hydrocarbon or halogenated alkyl group having 1 to 10 carbon atoms,
to a Horner-Wadsworth-Emmons reaction with an aldehyde compound of the following general formula (4):

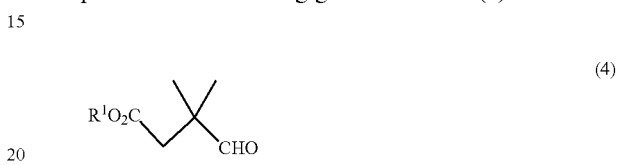

(4)

wherein $R^1$ is as defined above,
to form the compound (1).

4. The process for preparing the compound (2) according to claim 3, wherein $R^2$ and $R^4$ are an ethyl group and $R^3$ is a methyl group in the general formula (3).

5. A 1,3,3-trimethyl-1-butene-1,4-dicarboxylate compound of the following general formula (5):

(5)

wherein $R^1$ and $R^2$ each represent an ethyl group, and the wavy bond represents an E-configuration, a Z-configuration, or a mixture thereof.

* * * * *

UNITED STATES PATENT AND TRADEMARK OFFICE
CERTIFICATE OF CORRECTION

PATENT NO. : 11,518,729 B2  Page 1 of 1
APPLICATION NO. : 17/378936
DATED : December 6, 2022
INVENTOR(S) : Watanabe et al.

It is certified that error appears in the above-identified patent and that said Letters Patent is hereby corrected as shown below:

In the Specification

Column 1, Line 30: delete "a-necrodyl" and insert --α-necrodyl--

Column 1, Line 32: delete "y-necrodyl" and insert --γ-necrodyl--

Column 2, Line 5: delete "0-methoxycarbonylation" and insert --O-methoxycarbonylation--

Columns 9-10, Lines 20-35: delete the scheme of reactions and replace with the following:

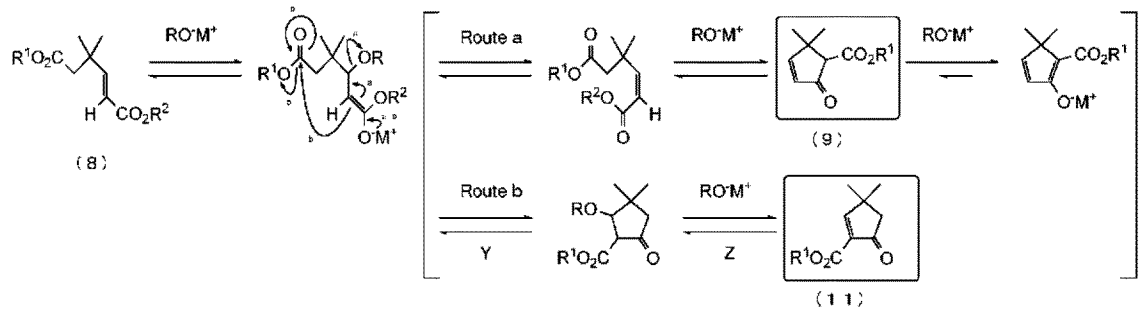

Column 10, Line 57: delete "Win" and insert --$R^3$ in--

Column 10, Line 61: delete "Win" and insert --$R^3$ in--

Signed and Sealed this
Ninth Day of May, 2023

Katherine Kelly Vidal
*Director of the United States Patent and Trademark Office*